United States Patent [19]

Schmidt et al.

[11] Patent Number: 4,595,486

[45] Date of Patent: * Jun. 17, 1986

[54] ELECTROCHEMICAL GAS SENSOR

[75] Inventors: John C. Schmidt, Baltimore; Donald N. Campbell, Timonium; Sandra B. Clay, Baltimore, all of Md.

[73] Assignee: Allied Corporation, Morristown, N.J.

[*] Notice: The portion of the term of this patent subsequent to Jun. 25, 2002 has been disclaimed.

[21] Appl. No.: 697,595

[22] Filed: Feb. 1, 1985

[51] Int. Cl.[4] .............................................. G01N 27/46
[52] U.S. Cl. .................................... 204/412; 204/431
[58] Field of Search ............... 204/412, 415, 1 T, 1 F, 204/431, 432

[56] References Cited

U.S. PATENT DOCUMENTS

| | | | |
|---|---|---|---|
| 3,776,832 | 12/1973 | Oswin et al. | 204/195 R |
| 3,966,579 | 6/1976 | Chang et al. | 204/415 X |
| 4,169,779 | 10/1979 | Tataria et al. | 204/412 |
| 4,184,937 | 1/1980 | Tataria | 204/195 R |
| 4,201,634 | 5/1980 | Stetter | 204/1 T |
| 4,268,370 | 5/1981 | Neti | 204/1 P X |
| 4,406,770 | 9/1983 | Chan et al. | 204/412 X |
| 4,525,266 | 6/1985 | Schmidt et al. | 204/432 X |
| 4,525,704 | 6/1985 | Campbell et al. | 204/412 X |

OTHER PUBLICATIONS

Publication J. A. Plambeck, *Electroanalytical Chemistry*, Wiley-Interscience, pp. 50-51, New York, N.Y. (1963).

Primary Examiner—John F. Niebling
Assistant Examiner—Nam X. Nguyen
Attorney, Agent, or Firm—Robert M. Trepp; Bruce L. Lamb

[57] ABSTRACT

An electrochemical gas sensor is described for detecting a gas constituent, for example hydrazine in a gas ambient incorporating an electrochemical cell including a reference electrode, counter electrode and sensing electrode spaced apart and with an electrolyte in contact with each electrode and comprising n-methyl-2-pyrrolidone and a salt soluble therein, for example tetraalkyl ammonium salt. The invention overcomes the problem of specificity, service life and operating temperature range associated with aqueous electrochemical gas sensors.

21 Claims, 2 Drawing Figures

ELECTROCHEMICAL GAS SENSOR

CROSS REFERENCES TO RELATED APPLICATIONS

This application is cross referenced to an application entitled "Electrochemical Gas Sensor" filed on Oct. 13, 1983 now abandoned having Ser. No. 541,650 by J. C. Schmidt, D. N. Campbell and S. B. Clay which describes an electrochemical gas sensor having a counter electrode and sensing electrode made of carbon in a three electrode system; also an electrolyte n-methyl-2-pyrrolidone and at least one conductive salt therein was described.

This application is further cross referenced to a U.S. application now U.S. Pat. No. 4,525,266 entitled "Electrochemical Gas Sensor" which was filed on Oct. 13, 1983 having Ser. No. 541,630 by J. C. Schmidt, D. N. Campbell and S. B. Clay and assigned to the assignee herein which describes an electrochemical gas sensor having a counter electrode of carbon, a sensor electrode and a reference electrode. Further an electrolyte n-methyl-2-pyrrolidone is described alone or with a conductive salt, such as tetrabutyl ammonium, tetrafluoroborate.

BACKGROUND OF THE INVENTION

1. Field of the Invention

This invention relates to electrochemical gas sensors and more particularly to a non-aqueous electrolyte for use in a three electrode chemical cell.

2. Description of the Prior Art

U.S. Pat. No. 3,776,832 to Oswin et al. which issued on Dec. 4, 1973 describes a three electrode electrochemical gas sensor which can be adapted to measure oxidizable or reducible gases, such as chlorine, CO, $Cl_2$ and hydrazine, as well as other gases. This particular known cell has two shortcomings. Firstly, it requires an aqueous electrolyte which has a limited service life due to evaporation of the electrolyte. Secondly, the temperature range within which the cell can operate is limited due to the possibility of freezing of the electrolyte.

The shortcomings noted above as a result of using an aqueous electrolyte have been recognized for some time. U.S. Pat. No. 4,184,937, which issued on Jan. 22, 1980 to H. Tataria et al. entitled "Electrochemical Cell for the Detection of Chlorine", describes a three electrode cell with a non-aqueous electrolyte consisting preferably of lithium perchlorate dissolved in an organic solvent selected from the group consisting of gamma-butyrolactone and propylene carbonate. The non-aqueous electrolyte has a considerably lower freezing point and vapor pressure than an aqueous electrolyte. The electrodes for use in the two or three electrode electrochemical cells are comprised of either gold or platinum black.

In U.S. Pat. No. 4,201,634, which issued on May 6, 1980 to J. R. Stetter entitled "Method for the Detection of Hydrazine", a three electrode electrochemical cell is described using an aqueous alkaline electrolyte (KOH) in contact with the sensing electrode. The sensing electrode comprises a noble metal catalyst bonded to a hydrophobic material to provide a diffusion electrode. The catalyst is described as rhodium or gold and the hydrophobic material is described as polytetrafluoroethylene.

In a publication by J. A. Plambeck, published in *Electro Analytical Chemistry*, Wiley-Interscience, pages 50–51, New York, N.Y. (1982), a potentiostat is described for maintaining a sensing electrode of an electrochemical cell at a fixed potential with respect to its reference electrode.

It is therefore desirable to provide an electrochemical gas sensor particularly suited for detecting hydrazine in a three electrode electrochemical cell where the electrolyte is n-methyl-2-pyrrolidone having tetraalkyl ammonium salt therein.

SUMMARY OF THE INVENTION

An electrochemical gas sensor for sensing is described comprising a reference electrode, a counter electrode and a sensing electrode spaced apart from each other, each said electrode including a noble metal, an electrolyte in the spaces between said electrodes in contact with each said electrode, said electrolyte including n-methyl-2-pyrrolidone and a salt soluble therein for example tetraalkyl ammonium salt, or lithium percholorate, a potentiostat for maintaining a predetermined voltage on said sensing electrode with respect to said reference electrode, and means responsive to said sensing electrode to provide an indication of the concentration of a specific gas in an ambient gas to be monitored.

DESCRIPTION OF THE PREFERRED EMBODIMENT

Figure 1:
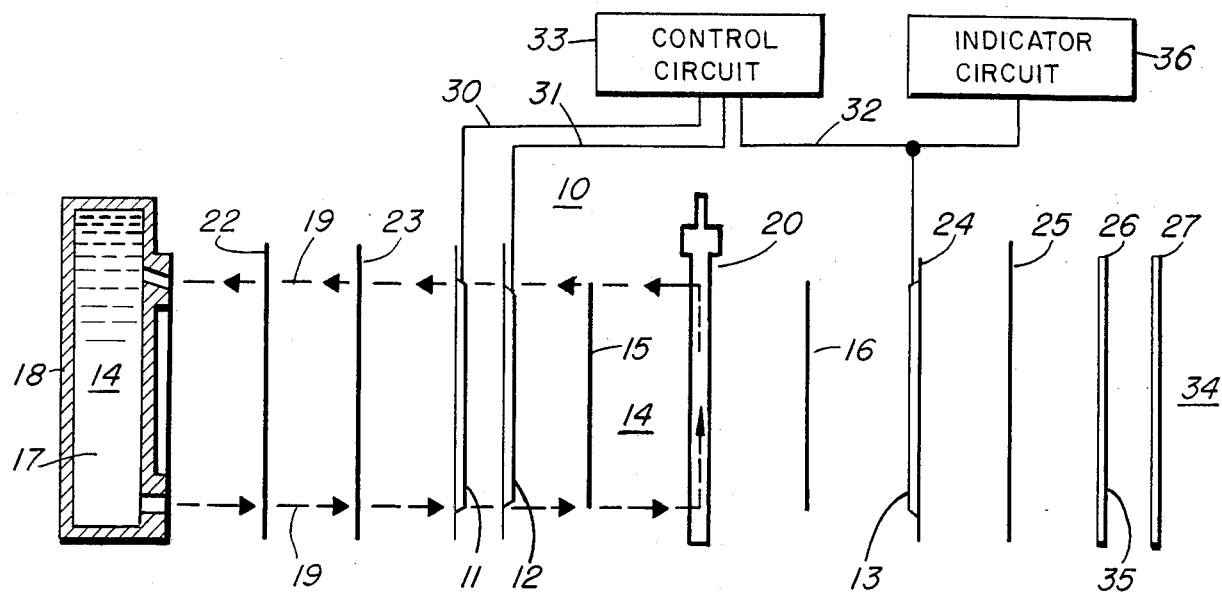
FIG. 1 is a schematic diagram of one embodiment of the invention.

Referring to FIG. 1, an electrochemical gas sensor 10 is shown. In FIG. 1 a three electrode chemical cell is shown comprising a reference electrode 11, a counter electrode 12 and a sensing electrode 13. As shown in FIG. 1 the electrodes are spaced apart from each other and may be constructed of a noble metal or alloy, for example gold, platinum, iridium or rhodium or be constructed of another material with a noble metal or alloy on the exterior surface. An electrolyte 14 is positioned in the spaces between electrodes 11–13 and in contact with electrodes 11–13 such as by means of filter paper 15 and 16, which may be fiberglass filter paper and wetted with electrolyte 14. Reference electrode 11 and counter electrode 12 may be positioned edge to edge to one another (side-by-side) and supported by one surface of electrode spacer 20.

Electrolyte 14 may be supplied from reservoir 17 having a housing 18. A wick 19 may furnish a fluid path for electrolyte 14 from reservoir 17 to electrodes 11–13 and filter papers 15 and 16. Electrolyte 14 may be, for example, n-methyl-2-pyrrolidone with a salt soluble therein for example tetraalkyl ammonium salts or lithium perchlorate. For example, electrolyte 14 may be a solution of n-methyl-2-pyrrolidone with a concentration of 0.005 to 2 molar of a tetraalkyl ammonium salt dissolved therein, such as tetraethylammonium tetrafluoroborate, also described by $(CH_3CH_2)_4NBF_4$. A typical concentration of tetraethylammonium tetrafluoroborate is a 0.2 molar solution.

As shown in FIG. 1 electrochemical gas sensor 10 also includes a gasket 22, a polypropylene (PPE) membrane 23, a porous membrane 24 which may be, for example, tetrafluoroethylene, a gasket 25 and metal frame 26. A convection barrier 27 which may, for example, be tetrafluoroethylene functions to reduce sensor noise caused by convection in the ambient gas. The various elements shown in FIG. 1 may be assembled as shown and positioned much closer together, so that the wide spaces shown in FIG. 1 do not occur in the assembled electrochemical gas sensor 10. In fact, electrical contact of electrodes 11–13 may be made by means of electrode spacer 20 and to respective leads 30–32. A control circuit 33 is coupled to leads 30–32 to provide a predetermined voltage on sensing electrode 13 with respect to reference electrode 11. Typically, control circuit 33 performs this function by providing current to counter electrode 12 which travels through the electrolyte 14 to sensor 13. Control circuit 33 may be a temperature compensated potentiostat, well known in the art. Indicator circuit 36 functions to measure the current to sensing electrode 13 over lead 32 and to provide an output signal indicative of the concentration of a specific gas, such as hydrazine, in an ambient 34 to be monitored.

For a more detailed description of the control circuit and indicator circuit 36, reference is made to a patent application now U.S. Pat. No. 4,525,266 entitled "Electrochemical Gas Sensor" having U.S. Ser. No. 541,630, which was filed on Oct. 13, 1983 by the inventors herein and assigned to the assignee herein, which is incorporated herein by reference.

In operation, ambient gas 34 passes through convection barrier 27 through a hole 35 in metal frame 26 and gasket 25 to sensing electrode 13 after passing through porous membrane 24. Sensing electrode 13 is at a predetermined potential, such as in the range from −700 mv to +500 mv, with respect to reference electrode 11. For sensing hydrazine, it is desirable to have sensing electrode 13 at −100 mv±5 mv. An electrochemical reaction involving specific gas constituents of ambient gas 34 occurs at sensing electrode 13. The reaction causes an electric current on lead 32 which is detected by indicator circuit 36.

Figure 2:
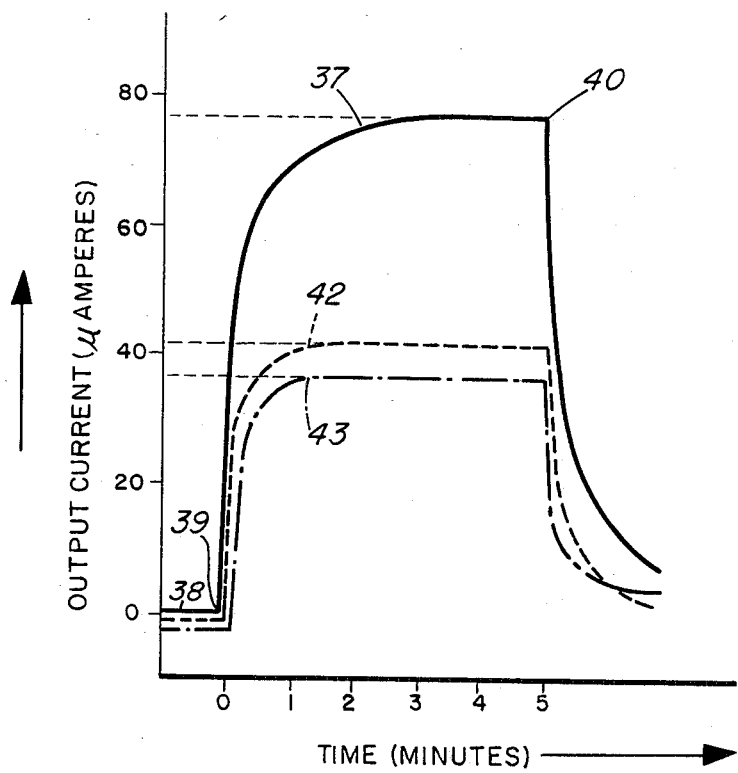
FIG. 2 is a graph showing a typical response of an electrochemical gas sensor in accordance with the embodiment of FIG. 1.

FIG. 2 is a graph showing the output current from sensing electrode 13 on lead 32 as a function of time before and after electrochemical gas sensor 10 is exposed to low levels of the hydrazines. In FIG. 2 the ordinant represents current in microamperes and the abscissa represents time in minutes. Curve 37 shows the response of electrochemical gas sensor 10 to ambient gas 34 having two parts per million of hydrazine ($NH_2NH_2$). Curve portion 38 of curve 37 represents when no hydrazine was present in ambient gas 34. At point 39 corresponding to about 0 minutes hydrazine gas was introduced into ambient gas 34 at a concentration of approximately two parts per million. At point 40 on curve 37 hydrazine was removed from ambient gas 34, which corresponds to about 5 minutes. As shown in FIG. 2, curve 37 rises to a value of 77 microamps in 3 minutes.

Curve 42 shows the response of electrochemical gas sensor 10 to an ambient gas 34 with six parts per million of unsymmetrical dimethyl hydrazine (UDMH). Curve 43 shows the response of electrochemical gas sensor 10 to an ambient gas 34 having two parts per million of monomethyl hydrazine (MMH). The UDMH and MMH gas was introduced into ambient gas 34 at approximately 0 minutes and removed at approximately 5 minutes as shown in FIG. 2. Curve 42 shows that electro-chemical gas sensor 10 had an output current of a little more than 40 microamps after 1 minute of exposure to UDMH. Curve 43 shows that electrochemical gas sensor 10 had an output current of approximately 36 microamps after 1.5 minutes as shown in FIG. 2.

The specificity of electrochemical gas sensor 10 is improved over prior art sensors due to the utilization of a non-aqueous electrolyte comprising n-methyl-2-pyrrolidone and a tetraalkyl ammonium salt or other salt soluble in n-methyl-2-pyrrolidone. A summary of the response to 15 common interferents of a prior art aqueous sensor and of the non-aqueous electrochemical sensor 10 shown in FIG. 1 is shown in table 1.

TABLE 1

| Interferent Gas Tested | Concentration Tested (PPM) | Response of Prior Art Aqueous Sensor | Response of Non-Aqueous Sensor |
|---|---|---|---|
| 1. Carbon Monoxide | 56 | No response | No response |
| 2. Methane | 900,000 | Moderate | No response |
| 3. Ethylene | 9,600 | Strong | No response |
| 4. Methanol | 201 | Strong | No response |
| 5. Ethanol | 100 | Strong | No response |
| 6. Acetone | 202 | Strong | No response |
| 7. Hydrogen Sulfide | 10 | Strong | Strong |
| 8. Methyl Mercaptan | 10 | Strong | Strong |
| 9. Sulfur Dioxide | 10 | Moderate | Moderate |
| 10. Nitrogen Dioxide | 50 | Strong | Negligible |
| 11. Ammonia | 230 | Moderate | Moderate |
| 12. Diethylamine | 391 | Strong | Negligible |
| 13. Triethylamine | 65 | Strong | Negligible |
| 14. Hydrogen Cyanide | 10 | Strong | Negligible |
| 15. Carbon Dioxide | 900,000 | No response | No response |

In Table 1 the response is given as strong, moderate or negligible at room temperature. A strong response to hydrazine corresponds to an interferent sensitivity of less than 100. A moderate response to hydrazine corresponds to an interferent sensitivity of between 100 and 1000. A negligible response to hydrazine corresponds to an interferent sensitivity of greater than 1000. The interferent sensitivity is defined by the ratio of the instrument (electrochemical sensor) response to hydrazine to the same instrument response to the same concentration of a given interferent. Thus, a strong response to hydrogen sulfide, number 7 in Table 1, corresponds to an instrument response to hydrazine over the instrument response to an interferent hydrogen sulfile of less than 100. A negligible response to nitrogen dioxide, number 10 in Table 1, corresponds to an instrument response to hydrazine over the instrument response to nitrogen dioxide of at least 1000 times.

Referring to Table 1, items 3–6, ethylene, methanol, ethanol and acetone generate a strong response in prior art aqueous sensors, while generating no response in the non-aqueous electrochemical gas sensor 10. A sensor which provides no response to ethylene, methanol, ethanol and acetone is a major advance in the art since these materials are used as solvents in many areas where the hydrazines ($NH_2NH_2$, MMH, and UDMH) constitute a threat to personnel. Further, the electrochemical gas sensor 10 is also less sensitive than prior art aqueous sensors to diethylamine, triethylamine and hydrogen cyanide, numbers 12–14 in Table 1, as well as nitrogen dioxide, number 10, in Table 1.

A further advantage by using the electrolyte n-methyl-2-pyrrolidone is that electrochemical gas sensor 10 may have a longer service life since n-methyl-2-pyrrolidone evaporates much more slowly than prior art aqueous electrolytes used in prior art sensors. This is due to the fact that n-methyl-2-pyrrolidone has a vapor pressure of 0.3 mm of mercury, while water has a vapor pressure of 18 mm of mercury at ambient room temperature. Further, n-methyl-2-pyrrolidone has a lower freezing temperature than the electrolyte in most aqueous sensors.

An electrochemical gas sensor has been described comprising a reference electrode, a counter electrode and a sensing electrode spaced apart from each other, wherein each electrode may be a noble metal or alloy, an electrolyte in the space between the electrodes in contact with each electrode, the electrolyte including n-methyl-2-pyrrolidone and a tetraalkyl ammonium salt or another salt soluble in n-methyl-2-pyrrolidone for example lithium perchlorate. A potentiostat provides a circuit for maintaining a predetermined voltage on the sensing electrode with respect to the reference electrode and an indicator circuit senses the electric current from the sensing electrode to provide an indication of the concentration of a gas constitutent in an ambient gas to be monitored.

The invention claimed is:

1. An electrochemical gas sensor comprising: a reference electrode, a counter electrode and a sensing electrode spaced apart from each other, an electrolyte in the spaces between said electrodes in contact with each said electrodes, said electrolyte including n-methyl-2-pyrrolidone and a salt soluble therein, circuit means for maintaining a predetermined voltage on said sensing electrode with respect to said reference electrode, and means responsive to electric current from said sensing electrode to provide an indication of the concentration of a gas in an ambient to be monitored.

2. The electrochemical gas sensor of claim 1 wherein said reference and sensing electrode includes a noble metal.

3. The electrochemical gas sensor of claim 1 wherein said sensing electrode includes platinum.

4. The electrochemical gas sensor of claim 1 wherein said sensing electrode includes iridium.

5. The electrochemical gas sensor of claim 1 wherein said sensing electrode includes rhodium.

6. The electrochemical gas sensor of claim 1 wherein the concentration of said salt soluble therein is in the range from 0.005 to 2 molar solution.

7. The electrochemical gas sensor of claim 1 wherein said salt soluble therein includes tetraalkyl ammonium salt.

8. The electrochemical gas sensor of claim 7 wherein the concentration of said tetraalkyl ammonium salt is in the range from 0.005 to 2 molar solution.

9. The electrochemical gas sensor of claim 7 wherein said tetraalkyl ammonium salt includes tetraethylammonium tetrafluoroborate.

10. The electrochemical gas sensor of claim 1 wherein said electrolyte includes a 0.2 molar solution of tetraethylammonium tetrafluoroborate in n-methyl-2-pyrrolidone.

11. The electrochemical gas sensor of claim 1 wherein said circuit means maintains said predetermined voltage at $-100$ millivolts $\pm 5$ millivolts on said sensing electrode with respect to said reference electrode for detecting hydrazine, monomethyl hydrazine or unsymmetrical dimethyl hydrazine in said ambient.

12. The electrochemical gas sensor of claim 1 wherein said salt soluble therein includes lithium perchlorate.

13. An electrochemical cell comprising: a reference electrode, a counter electrode and a sensing electrode spaced apart from each other, and an electrolyte in the spaces between said electrodes in contact with each said electrodes, said electrolyte including n-methyl-2-pyrrolidone and a tetraalkyl ammonium salt.

14. The electrochemical cell of claim 13 wherein said reference and sensing electrode includes a noble metal.

15. The electrochemical cell of claim 13 wherein said sensing electrode includes platinum.

16. The electrochemical cell of claim 13 wherein said sensing electrode includes iridium.

17. The electrochemical cell of claim 13 wherein said sensing electrode includes rhodium.

18. The electrochemical cell of claim 13 wherein the concentration of said tetraalkyl ammonium salt is in the range from 0.005 to 2 molar solution.

19. The electrochemical cell of claim 1 wherein said tetraalkyl ammonium salt includes tetraethylammonium tetrafluoroborate.

20. The electrochemical cell of claim 19 wherein said electrolyte includes a 0.2 molar solution of tetraethylammonium tetrafluoroborate.

21. An electrochemical cell comprising: a reference electrode, a counter electrode and a sensing electrode spaced apart from each other, and an electrolyte in the spaces between said electrodes in contact with each said electrodes, said electrolyte including n-methyl-2-pyrrolidone and lithium perchlorate.

* * * * *